United States Patent [19]

Rohling

[11] Patent Number: 5,680,861
[45] Date of Patent: Oct. 28, 1997

[54] MODULAR SUBJECT POSITIONING SYSTEM FOR MEDICAL IMAGING

[75] Inventor: Kenneth William Rohling, Burnt Hills, N.Y.

[73] Assignee: General Electric Company, Schenectady, N.Y.

[21] Appl. No.: 678,583

[22] Filed: Jul. 8, 1996

[51] Int. Cl.$^6$ ............................................. A61B 6/00
[52] U.S. Cl. ........................... 128/653.1; 128/653.2; 378/208
[58] Field of Search ............... 128/653.1, 653.2, 128/653.5; 378/204, 208, 163, 195; 324/318, 322, 321

[56] References Cited

U.S. PATENT DOCUMENTS

| 5,349,956 | 9/1994 | Bonutti | 128/653.1 |
| 5,517,990 | 5/1996 | Kalfas et al. | 128/653.1 |

*Primary Examiner*—Marvin M. Lateef
*Assistant Examiner*—Eleni Mantis Mercader
*Attorney, Agent, or Firm*—Lawrence P. Zale; Marvin Snyder

[57] ABSTRACT

An adjustable subject positioning device employs a 'pegboard' in which supports may be placed in a variety of locations. The supports hold various portions of the subject in order to position the subject such that the subject is in the position which accentuates an abnormality. An example would be to seat the subject and adjust the support such that the subject is in a sitting position with his upper torso bending over with his head towards his knees. This would accentuate bulges in disks between vertebrae. Once in this position, medical imaging may be accomplished making the abnormality much more visible than if the subject were in a prone position. Additionally, sensors connected to a position calculation device may store a representation of the where the supports were located during the image acquisition, and an indication of the locations of these supports be played back during viewing of the image. This allows the observer to take into account the subject position during imaging for a more accurate indication of abnormalities.

6 Claims, 4 Drawing Sheets

MODULAR SUBJECT POSITIONING SYSTEM FOR MEDICAL IMAGING

BACKGROUND OF THE INVENTION

1. Field of the Invention

The present invention relates to medical imaging apparatuses and more particularly to devices which correctly position a subject for medical imaging.

2. Description of Related Art

In many different types of injuries or dysfunctions, the subject must be placed in a certain position to detect the abnormalities during medical imaging. Typically, in the past, the subject lays flat on a table and is imaged by either computed tomography (CT) magnetic resonance (MR) imaging, positron emission tomography (PET), etc., and the images acquired. In many types of spinal dysfunctions, it is difficult to discern nerves being pinched between bone in this position. Many subjects complain of pain only when bending, standing in a certain manner or twisting in a given way. Since many of the medical imaging devices are only set up to image patients as they lay on a table, it may be difficult to obtain an image when nerves are being pinched or compressed.

Also, the natural weight of the body causes internal structures, such as bone to have a different relation with respect to other structures within the body as the subject is in different positions. For example, as the subject stands, disks between vetebrae are compressed and spaces between the vertebrae are much different from those in which the patient is lying down.

As the subject bends to touch his toes spacing between the ventral and posterior regions of vertebra become uneven. This may cause disks to bulge in a posterior direction.

Currently there is a need for an adjustable subject positioning device which allow subjects to be oriented in a selected position such that images may be acquired of the patient in that position.

SUMMARY OF THE INVENTION

An adjustable patient positioning system intended for use within a medical imaging device employs at least one structure plate having a plurality of attachment points each capable of receiving and fastening a support structure.

Body support structures are removeably connected structure plates capable of receiving and supporting a portion of a patient causing said patient to be in a selected position desired for medical imaging.

A plurality of sensors are located within the structure plates to detect when a body support is connected to that location.

The information from the sensors is passed to a position calculation device which also receives the information from the sensors, and indicates the body support locations, or subject position during imaging. This may be displayed on the same display device which the medical imaging device is displaying and image, or displayed on a separate device.

OBJECTS OF THE INVENTION

It is an object of the present invention to hold a subject in a selected position during medical imaging.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE INVENTION

Prior to open magnetic resonance (MR) imaging systems, MR imaging was performed in a cylindrically-shaped magnet having an opening passing through the length of the cylindrical magnet for receiving the subject. The subject being imaged would lay flat on a table placed within the opening. Therefore, MR images could only be acquired of a subject, lying flat on a table. Many medical problems are not evident with the patient imaged in this position. The images would not indicate effects of pressure on structures when standing, or in various other positions.

Figure 1:
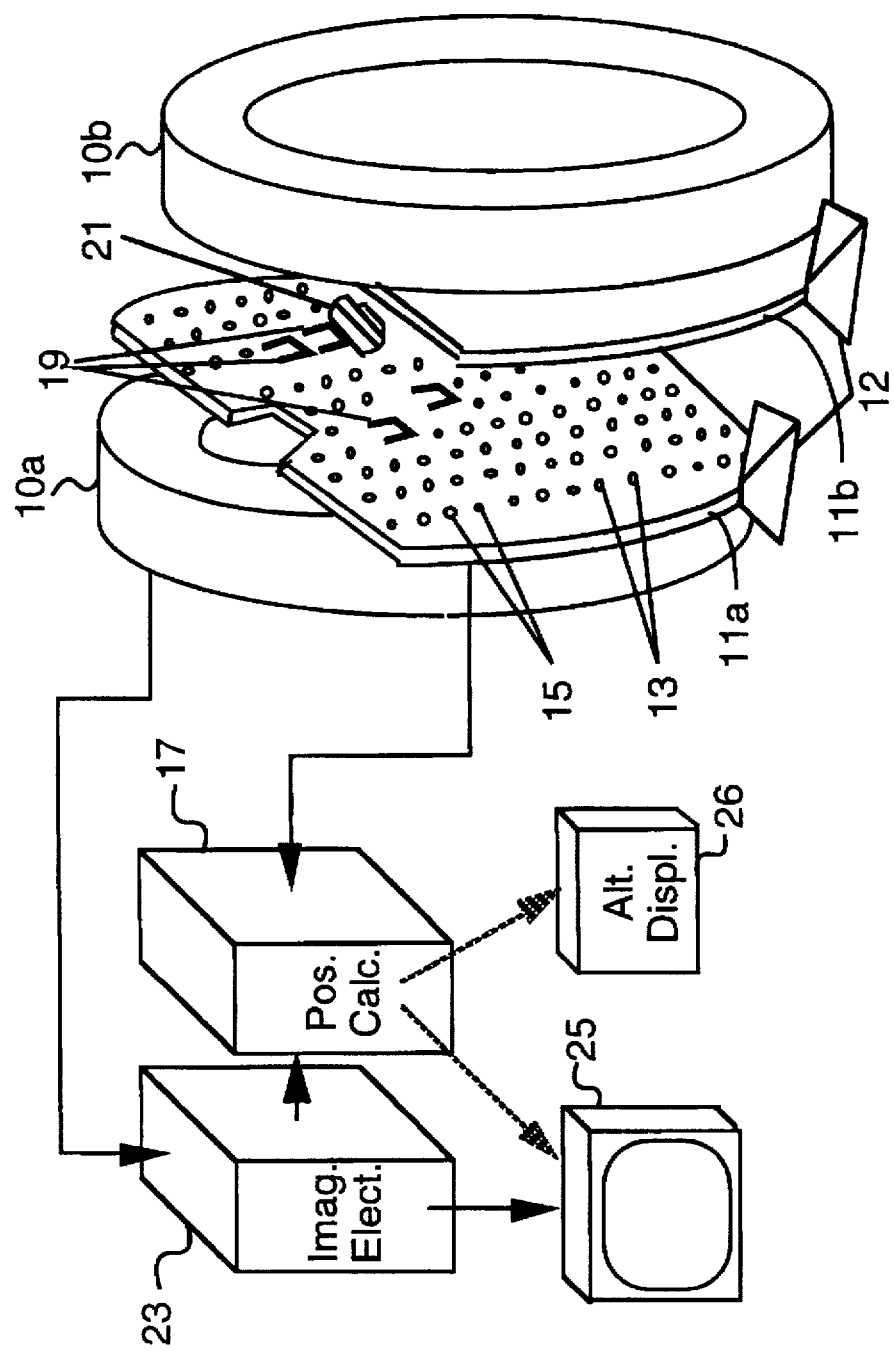
FIG. 1 is a simplified block diagram according to the present invention.

With the advent of open magnets, such as the one shown in FIG. 1, there is no longer the requirement that the subject be positioned lying down. FIG. 1 illustrates an open MR imaging system is shown having a pair of magnet rings 10a, 10b, imaging electronics 23 and a display 25. Gradient coils and radiofrequency (RF) transmit and receive coils are not visible from this view, but are part of the MR imaging system. This structure is a double doughnut, modified Helmholz coil imaging setup. Other open magnet setups may also be used.

A subject desired to be imaged, is positioned within the center of each ring 10a or 10b, between the rings.

At least one support plate, shown as 11a, 11b, may be free standing and have its own base 12, or secured to some portion of the MR imaging device.

Support plates 11a, 11b have a plurality of connection locations 13 for attaching body supports, to support the subject being imaged. The body supports are shown in greater detail in FIG. 2.

Connection locations 13 may also receive mounting brackets 19, to which the body supports modules may be attached. Body support modules may also be attached directly to support plates 11a, 11b.

Many conventional attachment methods may be used, such as, pegs that fit into the holes to secure the body support modules at a desired location.

Figure 2:
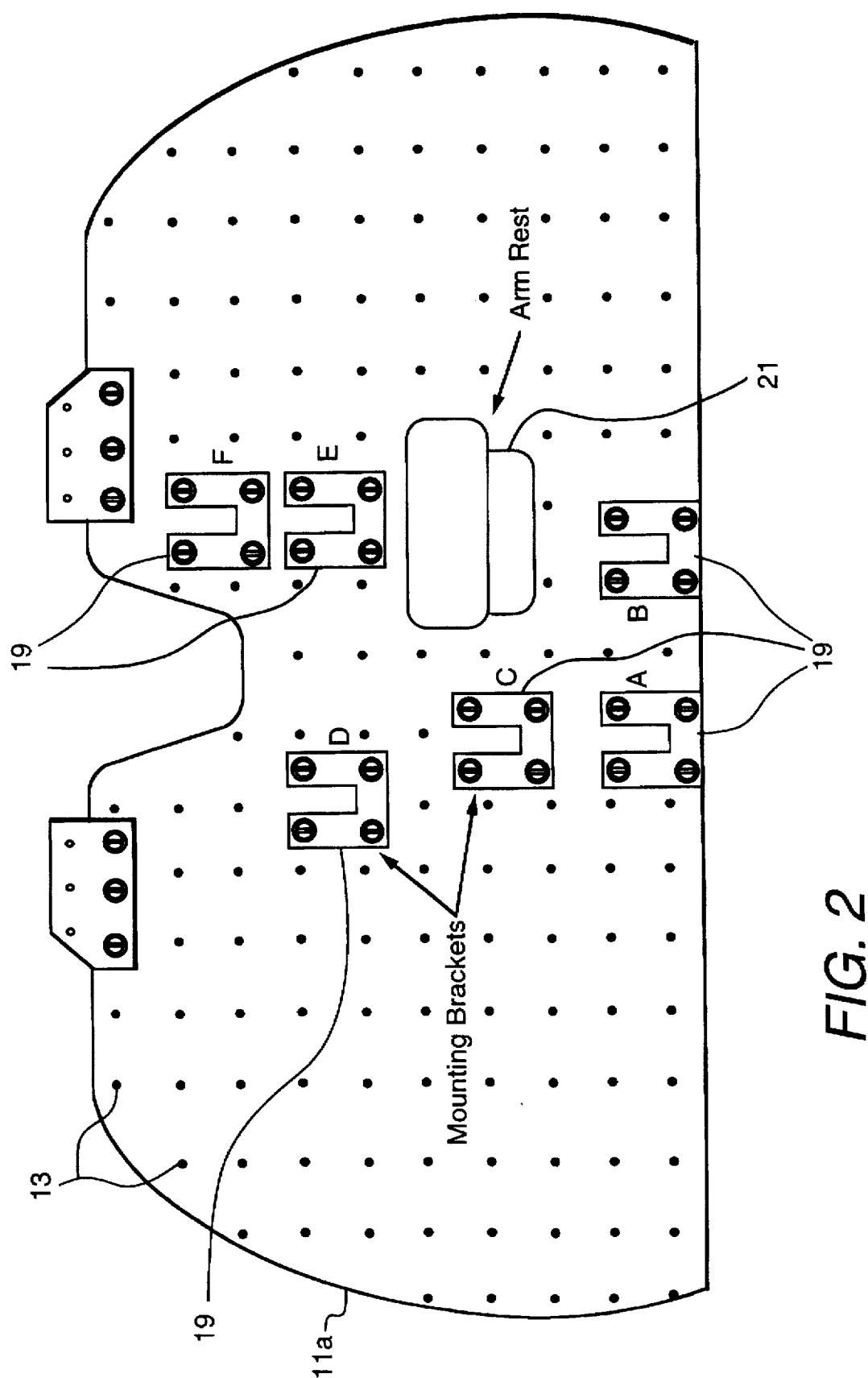
FIG. 2 is a more detailed figure of portions of FIG. 1.
Figure 3B:
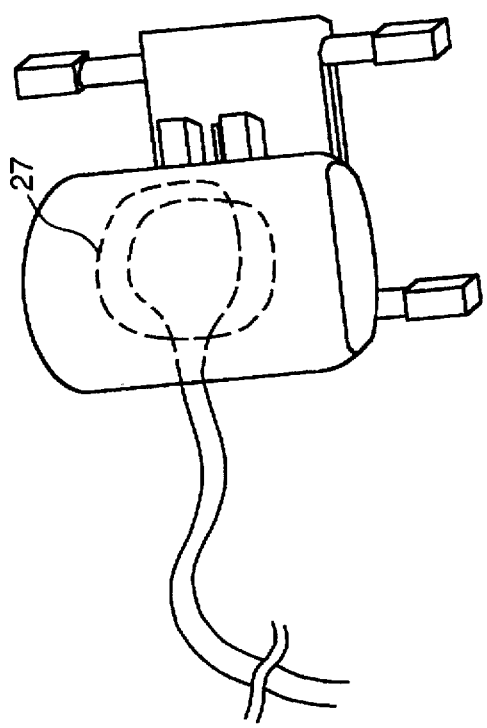
FIGS. 3a–3e illustrate various body supports which may be use in connection with the present invention.
Figure 3C:
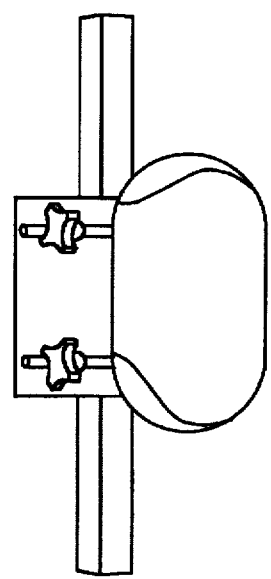
Figure 3A:
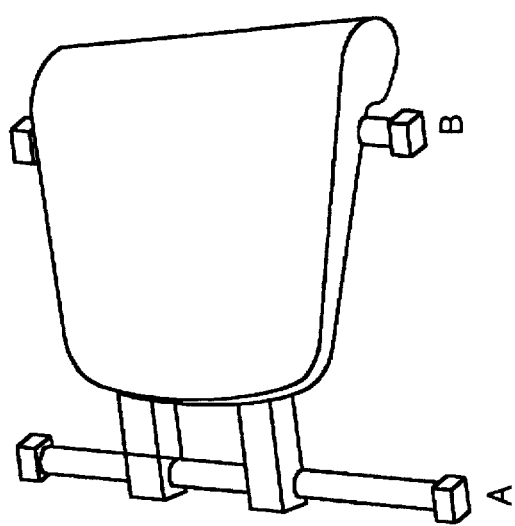
Figure 3D:
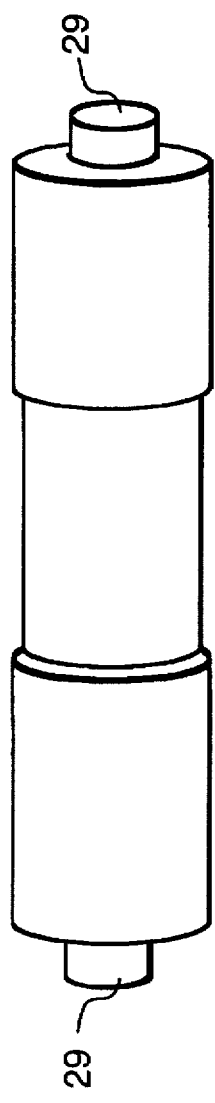
Figure 3E:
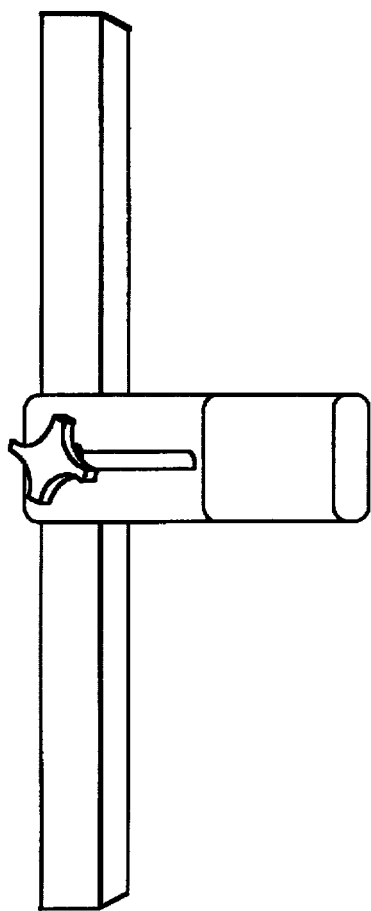

The body support modules may be, but are not limited to the following:

1) an adjustable seat module, shown in FIG. 3a where structures marked "A" and "B" fit into support brackets 19 also marked "A" and "B" of FIG. 2;

2) an adjustable back rest module, which may employ a magnetic resonance surface coil 27 embedded within its padding, connected by structures labeled "C" and "D" to the mounting brackets of FIG. 2 having the same labels;

3) an adjustable chest support module shown is shown in FIG. 3c supporting the chest of the subject; an arm rest module, such as 21 shown in FIGS. 1, 2, used to support the subject's arms;

5) a knee and leg support module such as that shown in FIG. 3d employs structures 29 to fit into mounting brackets of the support plates 11a, 11b;

6) an adjustable chin rest module of FIG. 3e, may be attached with structure labeled "F" to the support plate at the same label; and 7) the knee and leg support module of FIG. 3d may also double as a neck support module.

By properly positioning these support modules in support plates 11a, 11b, subject may be positioned in a sitting position with pressure on the vertebrae. Subject may also be positioned in a face down, "slumped-over" position by having a support underneath subject's abdomen with the head, neck, or chin support being lower than the abdomen support. Feet, knees or leg supports are also positioned lower than the abdomen support to cause the patient to be draped over the abdomen support. This position causes the posterior side of vertebrae to become spaced apart.

Patient may also be positioned in the opposite manner with abdomen facing up, a back support underneath the patient's back with the head and/or neck support and leg supports lower than the back support.

Patient may also be positioned such that an arm may be elevated to image a shoulder joint, knees may be flexed in order to correctly image knee joints and hips may be positioned to correctly image the hip joints.

Many times diagnosis of irregularities depends upon not only the image, but the position of the subject when the image was acquired. In an alternative embodiment, the present invention also provides position information along with, and corresponding to, the image information.

A plurality of sensors 15 are located within connection locations 13 of support plates 11a and 11b. These sensors are connected to a position calculation device 17.

In an alternative embodiment, the body supports could have optical encoding, or other identification means, for identifying which type of body support are connected to which sensor locations.

Also, in still another embodiment of the present invention, the sensors may be located within the body supports, and the support plates are encoded as to location. The sensors within the body supports, when attached to the support plate knows its location. This information is then passed to the position calculation device 17 by conventional means, including, but not limited to, hardwiring, radio communication, and inductive coupling.

Position calculation device 17 receives the sensor 15 information, and merges this information, or associates this information with the medical image information, such that the positions of body supports may be indicated with each specific medical image. The position of body supports, or a simulation of patient position, may be displayed on the same display 25 which medical imaging device displays the medical image, or on an alternative display 26, capable of showing support locations or patient position.

Sensor 15 information will then be stored corresponding to specific medical images indicating which type of body supports were used, and where these body supports were located when the medical image was acquired to aid in medical diagnosis.

The above example has been described in connection with magnetic resonance imaging, which is the preferred embodiment of the present invention. However, the present invention may also be equally be applied to other medical imaging systems. For example, the present modular patient handling system may be used in connection with ultrasound, computed tomography (CT) or positron emission tomography (PET).

While specific embodiments of the invention have been illustrated and described herein, it is realized that modifications and changes will occur to those skilled in the art. It is therefore to be understood that the appended claims are intended to cover all such modification s and changes as fall within the true spirit and scope of the invention.

What I claim is:

1. An adjustable patient positioning system intended for use within a medical imaging device comprising:

a) at least one structure plate secured in a substantially vertical position having a plurality of attachment points each capable of receiving and fastening a support structure;

b) at least one support structure removeably attached to the structure plate extending outward from the structure plate, capable of receiving and supporting a portion of a patient causing said patient to be in a selected position desired for medical imaging;

c) a medical imaging device for acquiring a medical image of a subject;

d) a plurality of sensors for determining when a support structure is attached to attachment points, which type of support is being attached and for creating a signal indicating the type and location of the attached support structures; and e) position calculation means coupled to the imaging device, for receiving the signal from the sensors, determining which support structures are used and their location at the time said medical image is acquired, and for storing this information associated with its corresponding acquired image.

2. The adjustable patient positioning system of claim 1 further comprising:

a playback means for indicating during image display, the type of support structure employed, the location of the support structure with each corresponding displayed image.

3. The adjustable patient positioning system of claim 1 wherein the position calculation means comprises a superposition means which superimposes a visual indication of the support structure attachment points on the medical image.

4. The adjustable patient positioning system of claim 1 wherein the position calculation means comprises a means capable of electronically storing an indication of the support structure attachment points along with an electronic representation of the medical image.

5. The adjustable patient positioning system of claim 1 wherein the body support means includes a magnetic resonance (MR) coil for receiving an MR response signal used in creating an MR image.

6. The adjustable patient positioning system of claim 1 wherein the support structures have pegs on them, and the structure plates having a corresponding plurality of holes, each sized to receive a peg of the support structures, allowing a plurality of possible support structure combinations and locations, resulting in a plurality of possible subject positions.

* * * * *